United States Patent [19]
Poetsch et al.

[11] Patent Number: 5,445,764
[45] Date of Patent: Aug. 29, 1995

[54] CYCLOBUTANE BENZENE DERIVATIVES

[75] Inventors: Eike Poetsch, Mühltal; Werner Binder, Dieburg; Volker Meyer, Gross-Zimmern; Ulrich Finkenzeller, Plankstadt; Bernhard Rieger, Münster, all of Germany

[73] Assignee: Merck Patent Gesellschaft mit beschrankter Haftung, Darmstadt, Germany

[21] Appl. No.: 256,684

[22] PCT Filed: Nov. 8, 1993

[86] PCT No.: PCT/EP93/03112
§ 371 Date: Jul. 20, 1994
§ 102(e) Date: Jul. 20, 1994

[87] PCT Pub. No.: WO94/12455
PCT Pub. Date: Jun. 9, 1994

[30] Foreign Application Priority Data

Nov. 21, 1992 [DE] Germany .................. 42 39 169.5

[51] Int. Cl.$^6$ .................. C09K 19/30; C09K 19/34; C07C 25/18; G02F 1/13
[52] U.S. Cl. .................. 252/299.63; 252/299.61; 252/299.62; 560/123; 570/127; 359/103
[58] Field of Search .................. 252/299.01, 299.63, 252/299.61, 299.62; 359/103; 560/123; 570/127

[56] References Cited

U.S. PATENT DOCUMENTS 5,384,072  1/1995  Poetsch et al. .................. 252/299.63

FOREIGN PATENT DOCUMENTS

| 449015 | 10/1991 | European Pat. Off. . |
| 4027923 | 3/1991 | Germany . |
| 2-85243 | 3/1990 | Japan . |
| 2155946 | 10/1985 | United Kingdom . |
| 8809322 | 12/1988 | WIPO . |
| 9108184 | 6/1991 | WIPO . |

Primary Examiner—Shean Wu
Attorney, Agent, or Firm—Millen, White, Zelano, & Branigan

[57] ABSTRACT

The invention relates to methylenecyclobutane benzene derivatives of the formula I

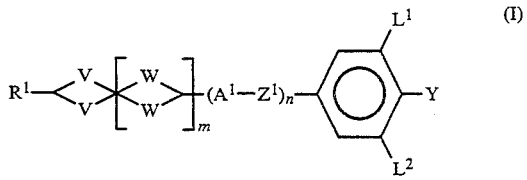

in which $R^1$, $A^1$, $Z^1$, $L^1$, $L^2$, m, V, W, Y and n have the meaning given in claim 1, and to their use as components of liquid-crystalline media for electrooptical displays.

12 Claims, No Drawings

CYCLOBUTANE BENZENE DERIVATIVES

SUMMARY OF THE INVENTION

The invention relates to cyclobutane benzene derivatives of the formula I

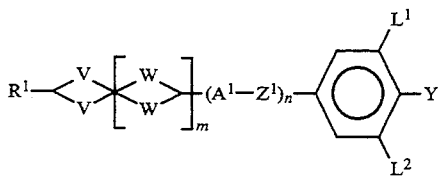

in which $R^1$ is alkyl or alkenyl having 1 to 16 carbon atoms, in which additionally one or more $CH_2$ groups may be replaced by —O—, or is a group of the formula

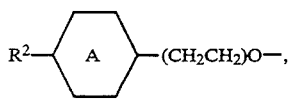

in which $R^2$ is alkyl or alkenyl having 1 to 16 carbon atoms,

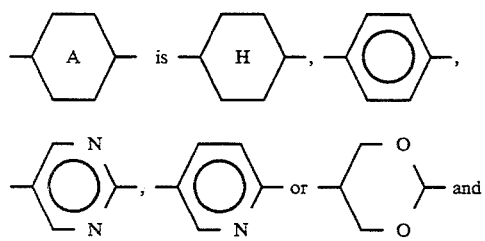

O is 0 or 1,

V and W are each $CH_2$ or $CH_2CH_2$, and when V is $CH_2CH_2$ m is 1, 2 or 3 and W is $CH_2$, $A^1$ is at each occurrence, independently of the others, 1,4-phenylene which is unsubstituted or substituted by 1 to 2 fluorine atoms, in which, in addition, one or two CH groups may be replaced by N, or is 1,4-cyclohexylene which is unsubstituted or substituted by a cyano group, and in which, in addition, one or two $CH_2$ groups may be replaced by O or S, or is thiadiazole-2,5-diyl, 1,4-bicyclo[2.2.2]-octylene, or a radical of the formula

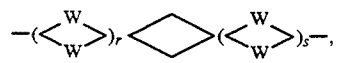

$L^1$ and $L^2$ are each independently of one another H or F, $Z^1$ is —CO—O—, —O—CO—, —CH$_2$O—, —OCH$_2$—, —CH$_2$CH$_2$—, —C≡C— or a single bond, Y is NCS, halogen or an alkyl, alkoxy, alkenyl or alkenyloxy group having 1 to 8 carbon atoms which is substituted by at least one fluorine and/or chlorine atom, and, if m=1, 2 or 3, is CN, or alkyl, or alkenyl having up to 16 carbon atoms, in which, in addition, 1 or more $CH_2$ groups may be reacted [sic] by —O—, m is 0, 1, 2 or 3, and n is 0, 1 or 2.

The invention relates furthermore to the use of these compounds as components of liquid-crystalline media and to liquid-crystal and electrooptical display elements containing the liquid-crystalline media according to the invention.

The compounds of the formula I can be used as components of liquid-crystalline media, especially for displays which are based on the principle of the twisted cell, including their highly twisted variants, for example STN or SBE, on the guest-host effect, on the effect of the deformation of aligned phases or on the effect of dynamic scattering.

The object underlying the invention was to discover new, stable, liquid-crystalline or mesogenic compounds which are suitable as components of liquid-crystalline media and which, in particular, have a comparatively low viscosity and a moderate positive dielectric anisotropy.

It has now been found that compounds of the formula I are ideally suited as components of liquid-crystalline phases. In particular, they possess comparatively low viscosities. They can be used to obtain stable liquid-crystalline phases with a broad mesophase range and advantageous values for the optical and dielectric anisotropy, which are at the same time notable for highly favorable values for specific resistance and low viscosities. By this means it is possible, in particular, to attain definite advantages in media for active matrix displays or supertwist displays.

Japanese Published Application JP 02 085 243 discloses benzonitrile derivatives of the formula

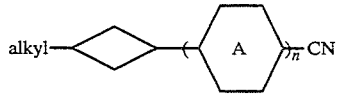

(n=1 or 2).

GB 21 55 946 encompasses cyclobutane derivatives of the formula I, but only describes cyclobutanecarboxylic esters. These esters, however, are not suitable for active matrix displays.

Other similar cyclobutane derivatives are described by:

DE-A 37 17 484:

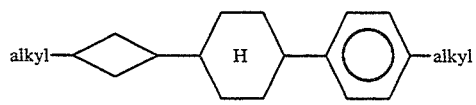

DE-A 39 29 524:

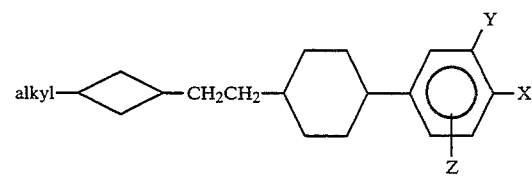

The general formula of WO 91/08184 includes benzene derivatives which have a group

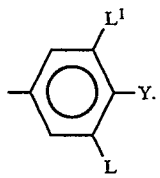

However, no cyclobutane derivatives are described therein.

Furthermore, the compounds described in the prior art only have moderate values for their optical anisotropy, whereas the compounds according to the invention possess distinctly lower optical anistropies and viscosities.

The provision of compounds of the formula I moreover represents, in quite general terms, a considerable broadening of the range of liquid-crystalline substances which are suitable, subject to various performance-related criteria, for the preparation of liquid-crystalline mixtures.

The compounds of the formula I possess a broad range of application. Depending on the choice of substituents these compounds can be used as base materials, of which liquid-crystalline phases are predominantly composed; however, it is also possible to add compounds of the formula I to liquid-crystalline base materials from other classes of compound, in order, for example, to influence the dielectric and/or optical anisotropy of such a dielectric and/or to optimize its threshold voltage and/or its viscosity.

The compounds of the formula I are colorless in the pure state and form liquid-crystalline mesophases in a temperature range which is favorable for electrooptical use. They are stable chemically, thermally and with respect to light.

The invention therefore relates to the compounds of the formula I.

Preferred embodiments of the present invention are:
a) derivatives in which m is 0;
b) derivatives in which $L^1$ and $L^2$ are identical and are F;
c) derivatives of the formula I1,

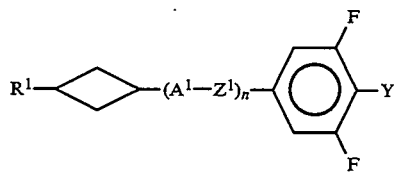

in which $R^1$, $A^1$, $Z^1$ and Y have the meaning given;
d) derivatives of the formula I2,

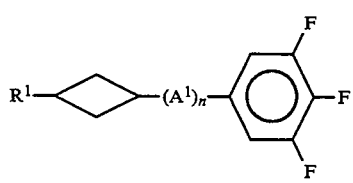

in which $R^1$ and $A^1$ have the meaning given;
e) derivatives of the formula I3,

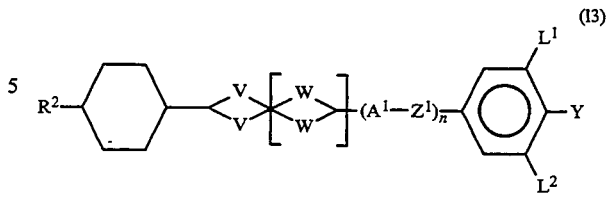

in particular of the formula I3a

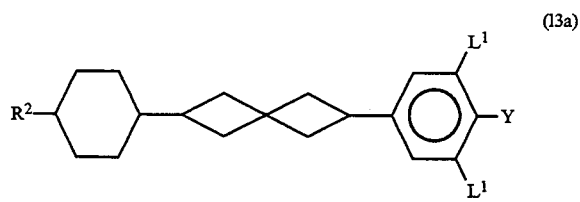

in which $R^2$, $A^1$, $Z^1$, V, W, $L^1$, $L^2$, m, n and Y have the meaning given.

The invention furthermore relates to the use of these compounds as components of liquid-crystalline media. The invention relates furthermore to liquid-crystalline media containing at least one compound; and to liquid-crystal display elements, especially electrooptical display elements, which contain such media, especially matrix liquid-crystal displays.

PREFERRED EMBODIMENTS

For simplicity, Cbu below is a radical of the formula

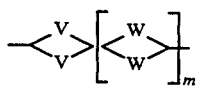

$A^3$ is a radical of the formula

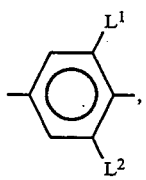

Cyc is a 1,4-cyclohexylene radical, Che is a 1,4-cyclohexylene radical, Dio is a 1,3-dioxane-2,5-diyl radical, Dit is a 1,3-dithiane-2,5-diyl radical, Phe is a 1,4-phenylene radical, PheF is a 1,4-phenylene radical which is mono- or disubstituted by fluorine, Pyd is a pyridine-2,5-diyl radical, Pyr is a pyrimidine2,5-diyl [sic] radical and Bi is a bicyclo[2.2.2]octylene radical, where Cyc and/or Phe are unsubstituted or may be mono- or disubstituted by F or CN.

The compounds of the formula I correspondingly include compounds containing two rings, of the subformula Ia:

$$R^1—Cbu—A^3—Y \qquad Ia$$

compounds containing three rings, of the subformulae Ib to Ig:

$$R^1—Cbu—A^1—A^3—Y \qquad Ib$$

| | |
|---|---|
| $R^1$—Cbu—$A^1$—Z1—$A^3$—Y [sic] | Ic |
| $R^2$—Cyc—Cbu—$A^3$—Y | Id |
| $R^2$—Dio—Cbu—$A^3$—Y | Ie |
| $R^2$—Cyc—CH$_2$CH$_2$—Cbu—$A^3$—Y [sic] | If |
| $R^2$—Dio—CH$_2$CH$_2$—Cbu—$A^3$—Y | Ig | and compounds containing four rings, of the subformulae Ih to Iq:

| | |
|---|---|
| $R^1$—Cbu—$A^1$—$A^1$—$A^3$—Y | Ih |
| $R^1$—Cbu—$A^1$—$Z^1$—$A^1$—$A^3$—Y | Ii |
| $R^1$—Cbu—$A^1$—$A^1$—$Z^1$—$A^3$—Y | Ij |
| $R^1$—Cbu—$A^1$—$Z^1$—$A^1$—$Z^1$—$A^3$—Y | Ik |
| $R^2$—Cyc—Cbu—$A^1$—$A^3$—Y | Il |
| $R^2$—Dio—Cbu—$A^1$—$A^3$—Y | Im |
| $R^2$—Cyc—Cbu—$A^1$—$Z^1$—$A^3$—Y | In |
| $R^2$—Dio—Cbu—$A^1$—$Z^1$—$A^3$—Y | Io |
| $R^2$—Cyc—CH$_2$CH$_2$—Cbu—$A^1$—$A^3$—Y | Ip |
| $R^2$—Dio—CH$_2$CH$_2$—Cbu—$A^1$—$A^3$—Y | Iq |

Of these compounds, those of the subformulae Ia, Ib, Ic, Id, Ie, If, Ig, Ii and Il are particularly preferred.

The preferred compounds of the subformula Ia include those of the subformulae Iaa and Iab:

| | |
|---|---|
| $R^1$—Cbu—Phe—Y | Iaa |
| $R^1$—Cbu—Phe—F—Y | Iab |

Of these compounds, those of the formula Iab are particularly preferred.

The preferred compounds of the subformula Ib include those of the subformulae Iba to Ibf:

| | |
|---|---|
| $R^1$—Cbu—Phe—Phe—Y | Iba |
| $R^1$—Cbu—Phe—PheF—Y | Ibb |
| $R^1$—Cbu—Cyc—Phe—Y | Ibc |
| $R^1$—Cbu—Cyc—PheF—Y | Ibd |
| $R^1$—Cbu—PheF—Phe—Y | Ibe |
| $R^1$—Cbu—PheF—PheF—Y | Ibf |

The preferred compounds of the subformula Ic include those of the subformulae Ica to Ich:

| | |
|---|---|
| $R^1$—Cbu—Phe—$Z^1$—Phe—Y | Ica |
| $R^1$—Cbu—Phe—$Z^1$—PheF—Y | Icb |
| $R^1$—Cbu—Cyc—$Z^1$—Phe—Y | Icc |
| $R^1$—Cbu—Cyc—$Z^1$—PheF—Y | Icd |
| $R^1$—Cbu—Dio—$Z^1$—Phe—Y | Ice |
| $R^1$—Cbu—Dio—$Z^1$—PheF—Y | Icf |
| $R^1$—Cbu—Pyd—$Z^1$—$A^3$—Y | Icg |
| $R^1$—Cbu—Pyr—$Z^1$—$A^3$—Y | Ich |

Of these compounds, those of the formulae Ica, Icb and Icc are particularly preferred.

The preferred compounds of the subformula Id include those of the subformulae Ida and Idb:

| | |
|---|---|
| $R^2$—Cyc—Cbu—Phe—Y | Ida |
| $R^2$—Cyc—Cbu—PheF—Y | idb |

The preferred compounds of the subformula Ie include those of the subformulae Iea and Ieb:

| | |
|---|---|
| $R^2$—Dio—Cbu—Phe—Y | Iea |
| $R^2$—Dio—Cbu—PheF—Y | Ieb |

In the compounds of the formulae above and below, the radicals $L^1$ and $L^2$ are identical or different from one another; they are preferably identical and are F.

The terminal group $R^1$—Cbu is preferably a group of the formulae 1 to 7:

= Cbu$^1$  1

= Cbu$^2$  2

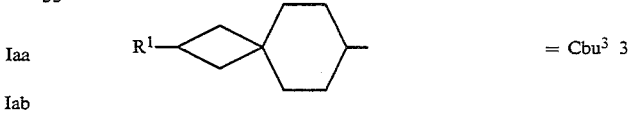

= Cbu$^3$  3

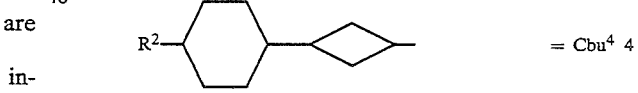

= Cbu$^4$  4

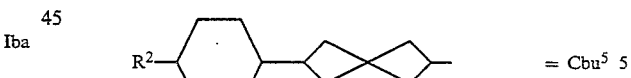

= Cbu$^5$  5

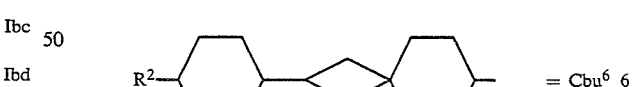

= Cbu$^6$  6

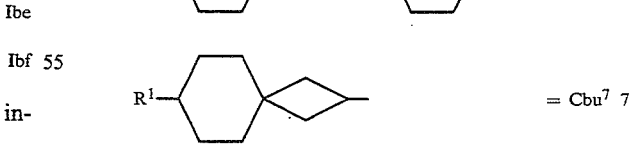

= Cbu$^7$  7 in which the radicals Cbu$^2$ and Cbu$^5$ are particularly preferred.

$A^1$ is preferably Phe, Cyc, Pyr or Dio. The compounds of the formula I preferably contain not more than one of the radicals Bi, Pyd, Pyr, Dio or Dit.

Also preferred are compounds of the formula I and of all subformulae in which $A^1$ and/or $A^3$ is 1,4-phenylene which is mono- or disubstituted by F. In particular these are 2-fluoro-1,4-phenylene, 3-fluoro-1,4-phenylene and 2,3-difluoro-1,4-phenylene, 2,6-difluoro-1,4-phenylene and 3,5-difluoro-1,4-phenylene.

Particularly preferred compounds of the formulae I are those in which $A^3$ is 1,4-phenylene which is unsubstituted or mono- or disubstituted by F.

The group $A^3$—Y is preferably:

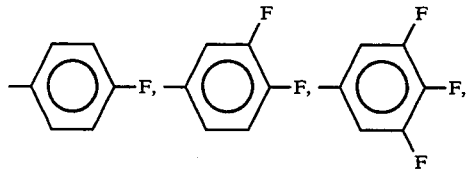

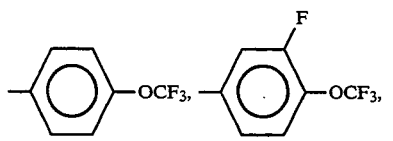

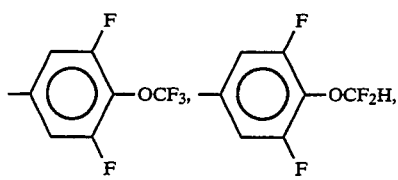

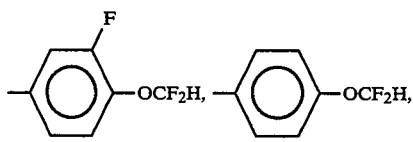

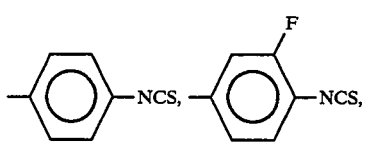

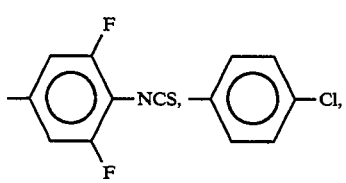

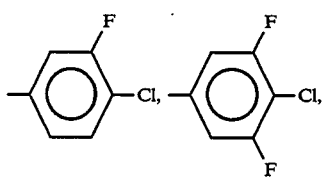

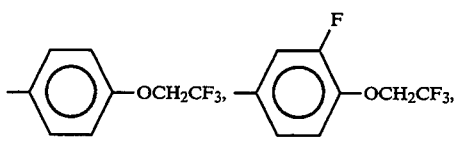

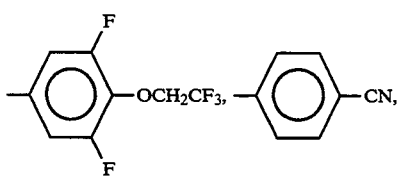

-continued

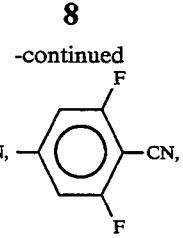

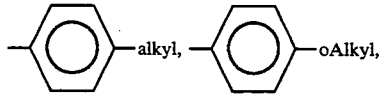

in which alkyl is alkyl having 1 to 16 carbon atoms.

Preferred radicals $A^3$ are those in which at least one of the ligands $L^1$ and $L^2$ is F, in particular in which $L^1$ and $L^2$ are F.

$Z^1$ is preferably a single bond, —CO—O—, —O—CO— and —CH$_2$CH$_2$—, with a secondary preference for —CH$_2$O—, —OCH$_2$—.

If $R^1$ or Y is an alkyl radical, then this radical may be straight-chain or branched. It is preferably straight-chain, has 2, 3, 4, 5 or 6 carbon atoms and is therefore preferably ethyl, propyl, butyl, pentyl or hexyl.

If $R^1$ or Y is an alkenyl radical, then this radical may be straight-chain or branched. It is preferably branched, has 2, 3, 4, 5 or 6 carbon atoms and is therefore vinyl, allyl, prop-1-enyl, but-1-(2- or 3-)enyl, pent-1-(2-, 3- or 4-)enyl, hex-1-(2-, 3-, 4- or 5-)enyl.

If Y is an alkoxy radical, then this radical is branched or straight-chain.

It is preferably straight-chain and is therefore preferably methoxy, ethoxy, propoxy, butoxy, pentyloxy or heptyloxy.

$L^1$ and $L^2$ are preferably identical and are F or H, especially F.

Among these compounds of the formula I and the subformulae, those are preferred in which at least one of the radicals they contain has one of the preferred meanings given.

In the compounds of the formula I those stereoisomers are preferred in which the rings Cyc and piperidine are trans-1,4-disubstituted. Those of the abovementioned formulae which contain one or more groups Pyd, Pyr, Dit and/or Dio in each case include the two 2,5-positional isomers.

Particularly preferred compounds of the formula I which contain a group of the formula 1 are those of the subformulae IIa to IIp:

| | |
|---|---|
| $R^1$—Cbu$^1$—Phe—F | IIa |
| $R^1$—Cbu$^1$—PheF—F | IIb |
| $R^1$—Cbu$^1$—Phe—NCS | IIc |
| $R^1$—Cbu$^1$—PheF—NCS | IId |
| $R^1$—Cbu$^1$—Phe—OCF$_3$ | IIe |
| $R^1$—Cbu$^1$—PheF—OCF$_3$ | IIf |
| $R^1$—Cbu$^1$—Phe—OCF$_2$H | IIg |
| $R^1$—Cbu$^1$—PheF—OCF$_2$H | IIh |
| $R^1$—Cbu$^1$—Cyc—Phe—F | IIi |
| $R^1$—Cbu$^1$—Cyc—PheF—F | IIj |

| | |
|---|---|
| R¹—Cbu¹—Cyc—PheF—NCS | I1k |
| R¹—Cbu¹—Cyc—Phe—NCS | I1l |
| R¹—Cbu¹—Cyc—Phe—OCF$_3$ | I1m |
| R¹—Cbu¹—Cyc—Phe—OCF$_2$H | I1n |
| R¹—Cbu¹—Cyc—PheF—OCF$_3$ | I1o |
| R¹—Cbu¹—Cyc—PheF—OCF$_2$H | I1p |

Particularly preferred compounds of the formula I which contain a group of the formula 2 are those of the subformulae I2a to I2x:

| | |
|---|---|
| R¹—Cbu²—Phe—F | I2a |
| R¹—Cbu²—PheF—F | I2b |
| R¹—Cbu²—Phe—NCS | I2c |
| R¹—Cbu²—PheF—NCS | I2d |
| R¹—Cbu²—Phe—OCF$_3$ | I2e |
| R¹—Cbu²—PheF—OCF$_3$ | I2f |
| R¹—Cbu²—Phe—OCF$_2$H | I2g |
| R¹—Cbu²—PheF—OCF$_2$H | I2h |
| R¹—Cbu²—Cyc—Phe—F | I2i |
| R¹—Cbu²—Cyc—PheF—F | I2j |
| R¹—Cbu²—Cyc—PheF—NCS | I2k |
| R¹—Cbu²—Cyc—Phe—NCS | I2l |
| R¹—Cbu²—Cyc—Phe—OCF$_3$ | I2m |
| R¹—Cbu²—Cyc—Phe—OCF$_2$H | I2n |
| R¹—Cbu²—Cyc—PheF—OCF$_2$H | I2o |
| R¹—Cbu²—Cyc—PheF—OCF$_3$ | I2p |
| R¹—Cbu²—Phe—alkyl | I2q |
| R¹—Cbu²—Phe—Oalkyl | I2r |
| R¹—Cbu²—Cyc—Phe—alkyl | I2s |
| R¹—Cbu²—Cyc—Phe—Oalkyl | I2t |
| R¹—Cbu²—Phe—CN | I2u |
| R¹—Cbu²—PheF—CN | I2v |
| R¹—Cbu²—CycPhe—CN | I2w |
| R¹—Cbu²—Cyc—PheF—CN | I2x |

Particularly preferred compounds of the formula I which contain a group of the formula 3 are those of the subformulae I3a to I3p:

| | |
|---|---|
| R¹—Cbu³—Phe—F | I3a |
| R¹—Cbu³—PheF—F | I3b |
| R¹—Cbu³—Phe—NCS | I3c |
| R¹—Cbu³—PheF—NCS | I3d |
| R¹—Cbu³—Phe—OCF$_3$ | I3e |
| R¹—Cbu³—PheF—OCF$_3$ | I3f |
| R¹—Cbu³—Phe—OCF$_2$H | I3g |
| R¹—Cbu³—PheF—OCF$_2$H | I3h |
| R¹—Cbu³—Cyc—Phe—F | I3i |
| R¹—Cbu³—Cyc—PheF—F | I3j |
| R¹—Cbu³—Cyc—PheF—NCS | I3k |
| R¹—Cbu³—Cyc—Phe—NCS | I3l |
| R¹—Cbu³—Cyc—Phe—OCF$_3$ | I3m |
| R¹—Cbu³—Cyc—Phe—OCF$_2$H | I3n |
| R¹—Cbu³—Cyc—PheF—OCF$_2$H | I3o |
| R¹—Cbu³—Cyc—PheF—OCF$_3$ | I3p |

Particularly preferred compounds of the formula I which contain a group of the formula 5 are those of the subformulae I5a to I5x:

| | |
|---|---|
| R²—Cbu⁵—Phe—F | I5a |
| R²—Cbu⁵—PheF—F | I5b |
| R²—Cbu⁵—Phe—NCS | I5c |
| R²—Cbu⁵—PheF—NCS | I5d |
| R²—Cbu⁵—Phe—OCF$_3$ | I5e |
| R²—Cbu⁵—PheF—OCF$_3$ | I5f |
| R²—Cbu⁵—Phe—OCF$_2$H | I5g |
| R²—Cbu⁵—PheF—OCF$_2$H | I5h |
| R²—Cbu⁵—Cyc—Phe—F | I5i |
| R²—Cbu⁵—Cyc—PheF—F | I5j |
| R²—Cbu⁵—Cyc—Phe—NCS | I5k |
| R²—Cbu⁵—Cyc—PheF—NCS | I5l |
| R²—Cbu⁵—Cyc—Phe—OCF$_3$— | I5m |
| R²—Cbu⁵—Cyc—PheF—OCF$_3$— | I5n |
| R²—Cbu⁵—Cyc—Phe—OCF$_2$H | I5o |
| R²—Cbu⁵—Cyc—PheF—OCF$_2$H | I5p |
| R²—Cbu⁵—Phe—CN | I5q |
| R²—Cbu⁵—PheF—CN | I5r |
| R²—Cbu⁵—CycPhe—CN | I5s |
| R²—Cbu⁵—Cyc—PheF—CN | I5t |
| R²—Cbu⁵—Cyc—Phe—Oalkyl | I5u |
| R²—Cbu⁵—Cyc—Phe—alkyl | I5v |
| R²—Cbu⁵—Phe—Oalkyl | I5w |

R²—Cbu⁵—Phe—alkyl   I5x

The 1,4-cyclohexenylene group preferably has the following structures:

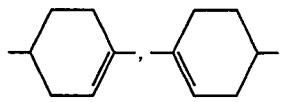

The compounds of the formula I are prepared by methods known per se, as described in the literature (e.g. in the standard works such as Houben-Weyl, Methoden der Organischen Chemie [Methods of Organic Chemistry], Georg-Thieme-Verlag, Stuttgart, under reaction conditions which are known and suitable for the reactions mentioned. In this context it is also possible to use variants which are known per se and not mentioned here in any more detail.

The compounds of the formula I in which m is 0 may be prepared, for example, in analogy in to that of Dobier et al. (J. Am. Chem. Soc. 107 (12) 3626–31 (1985)) by cycloaddition of allenes with styrene derivatives and subsequent hydrogenation (cf. Scheme I):

Scheme 1

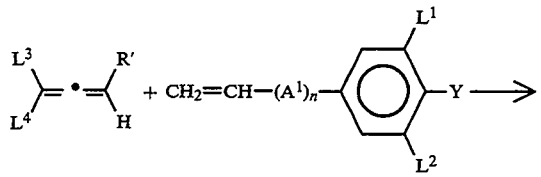

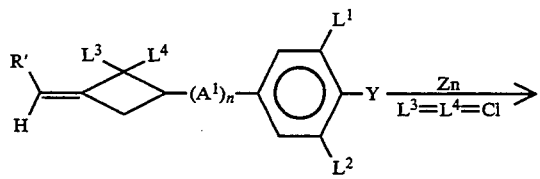

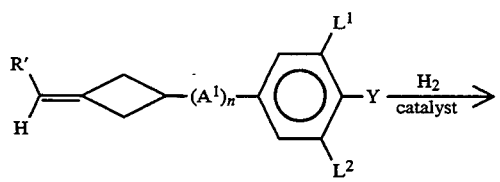

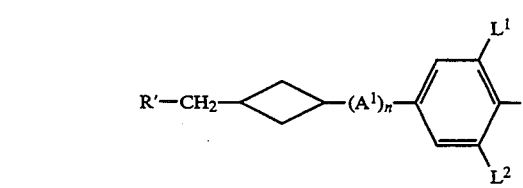

In addition, the compounds of the formula I can be prepared from the corresponding 3-substituted cyclobutanones by condensation with methane derivatives in accordance with C. Burton et al., Tetrahedron Lett. 29 (24), 3003–6 (1988) or J. Fried, et al., Tetrahedron Lett. 25, 4329 (1984) in the presence of a phosphine and subsequent hydrogenation (e.g. Schemes 2 to 5).

Scheme 2

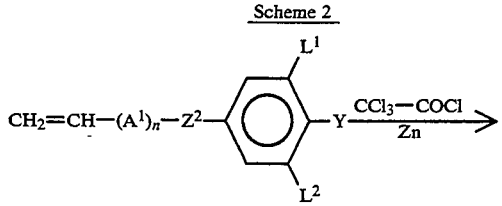

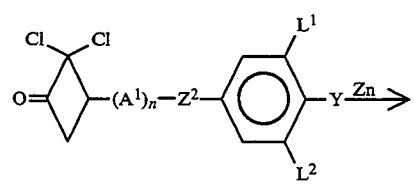

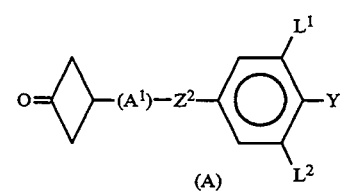

Scheme 3

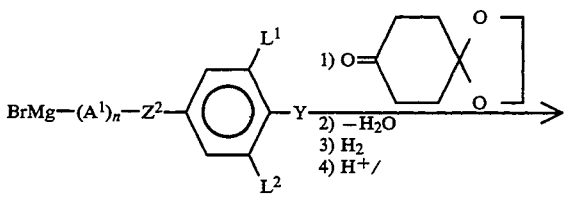

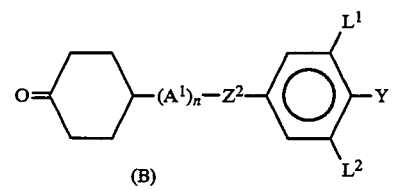

Scheme 4

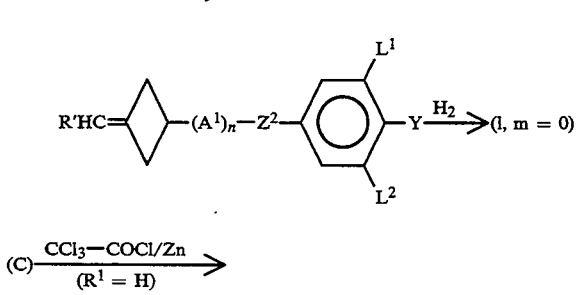

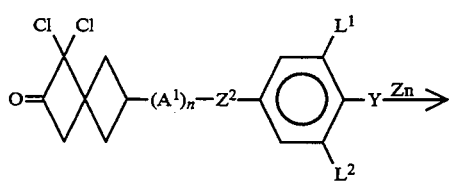

Scheme 4 -continued

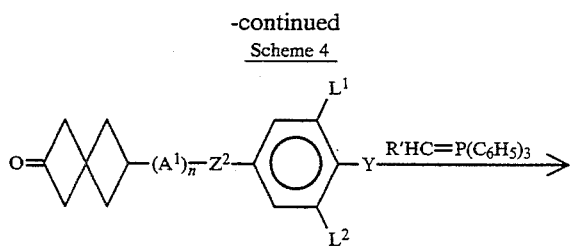

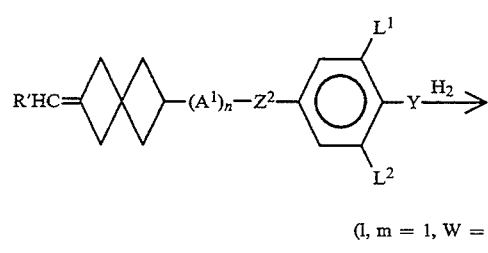

(l, m = 1, W = CH₂)

Scheme 5

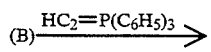

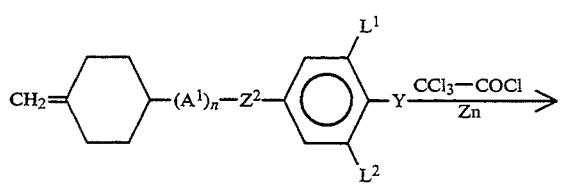

(l, m = 1, W = CH₂CH₂)

The compounds of the formula I3 can be prepared, for example, in accordance with Scheme 6-8.

Scheme 6

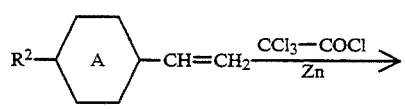

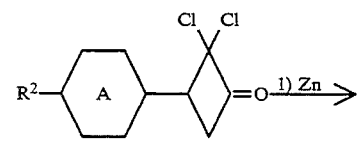

Scheme 6 -continued

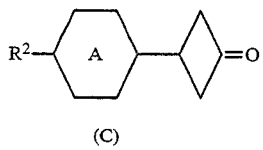

Scheme 7

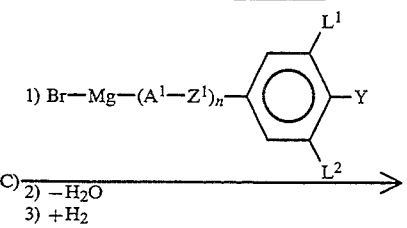

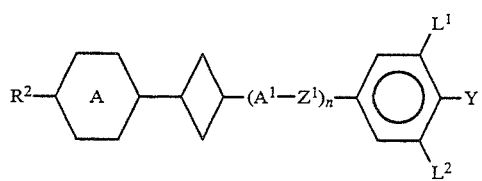

Scheme 8

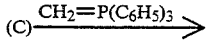

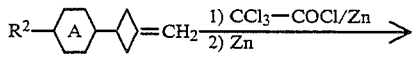

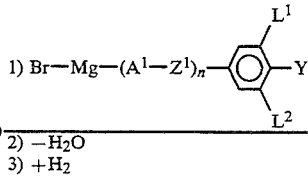

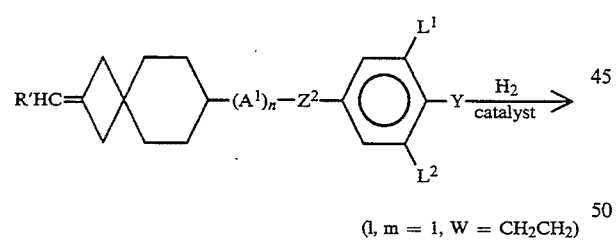

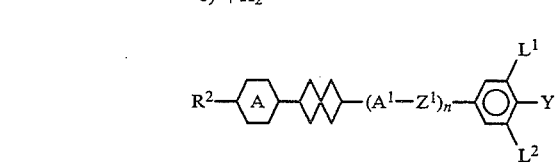

In addition, the compounds of the formula I can be prepared by reducing a compound which corresponds to the formula I except that, in place of hydrogen atoms, it contains one or more reducible groups and/or C—C bonds.

Suitable reducible groups which are preferred are carbonyl groups, especially keto groups, and also, for example, free or esterified hydroxyl groups or halogen atoms bonded to aromatic structures. Preferred starting materials for the reduction correspond to the formula I but, in place of a cyclohexane ring, may contain a cyclohexene ring or cyclohexanone ring and/or in place of a —CH₂CH₂— group may contain a —CH═CH— group and/or in place of a —CH₂— group may contain a —CO— group and/or in place of a hydrogen atom may contain an OH group which is free or functionally modified (e.g. in the form of its p-toluene sulfonate).

The reduction can be carried out, for example, by catalytic hydrogenation at temperatures of between approximately 0° and approximately 200° and at pressures of between approximately 1 and 200 bar in an inert solvent, for example an alcohol such as methanol, ethanol or isopropanol, an ether such as tetrahydrofuran (THF) or dioxane, an ester such as ethyl acetate, a carboxylic acid such as acetic acid or a hydrocarbon such as cyclohexane. Suitable catalysts are advantageously noble metals such as Pt or Pd, which may be employed in the form of oxides (e.g. $PtO_2$, PdO), on a support (e.g. Pd on carbon, calcium carbonate or strontium carbonate) or in finely divided form.

Ketones can also be reduced by the methods of Clemmensen (with zinc, amalgamated zinc or tin and hydrochloric acid, advantageously in aqueous-alcoholic solution or in heterogeneous phase with water/toluene at temperatures of between approximately 80° and 120°) or of Wolff-Kishner (with hydrazine, advantageously in the presence of alkali such KOH or NaOH in a high-boiling solvent such as diethylene glycol or triethylene glycol at temperatures of between approximately 100° and 200°) to give the corresponding compounds of the formula I which contain alkyl groups and/or —$CH_2CH_2$— bridges.

Reductions with complex hydrides are also possible. For example, arylsulfonyloxy groups can be reductively removed using $LiAlH_4$ and in particular p-toluenesulfonyloxymethyl groups can be reduced to methyl groups, advantageously in an inert solvent such as diethyl ether or THF at temperatures of between approximately 0° and 100°. Double bonds can be hydrogenated using $NaBH_4$ or tributyltin hydride in methanol.

Compounds of the formula I which correspond to the formula I except that, in place of 1,4-phenylene radicals, they possess 1,4-cyclohexenylene radicals, can be oxidized, for example, using DDQ (dichlorodicyanobenzoquinone) in a suitable solvent.

Esters of the formula I can also be obtained by esterification of corresponding carboxylic acids (or their reactive derivatives), especially of the formula IV, using alcohols or phenols (or their reactive derivatives), in particular of the formula V, or by the DCC method (DCC=dicyclohexylcarbodiimide).

The corresponding carboxylic acids and alcohols or phenols are known or can be prepared in analogy to known processes.

Particularly suitable reactive derivatives of the carboxylic acids mentioned are the acid halides, especially the chlorides and bromides, and also the anhydrides, including, for example, mixed anhydrides, azides or esters, in particular alkyl esters having 1-4 carbon atoms in the alkyl group.

Particularly suitable reactive derivatives of the alcohols and phenols mentioned are the corresponding metal alcoholates or phenolates, preferably of an alkali metal such as sodium or potassium.

The esterification is advantageously carried out in the presence of an inert solvent. Particularly suitable such solvents are ethers such as diethyl ether, di-n-butyl ether, THF, dioxane or anisole, ketones such as acetone, butanone or cyclohexanone, amides such as DMF or phosphoric acid hexamethyltriamide, hydrocarbons such as benzene, toluene or xylene, halogenated hydrocarbons such as carbon tetrachloride, dichloromethane or tetrachloroethylene, and sulfoxides such as dimethyl sulfoxide or sulfolane.

For the preparation of nitriles of the formula I it is possible to dehydrate corresponding acid amides, for example those in which there is a $CONH_2$ group in place of the radical CN. The amides can be obtained, for example, from corresponding esters or acid halides by reaction with ammonia. Examples of suitable water-eliminating agents are inorganic acid chlorides such as $SOCl_2$, $PCl_3$, $PCl_5$, $POCl_3$, $SO_2Cl_2$, $COCl_2$, and also $P_2O_5$, $P_2S_5$, $AlCl_3$ (for example as a double compound with NaCl), aromatic sulfonic acids and sulfonyl halides. This procedure can be carried out in the presence or absence of an inert solvent at temperatures of between approximately 0° and 150°; examples of suitable solvents are bases such as pyridine or triethylamine, aromatic hydrocarbons such as benzene, toluene or xylene, or amides such as DMF.

For the preparation of the abovementioned nitriles of the formula I it is also possible to react corresponding acid halides, preferably the chlorides, with sulfamide, advantageously in an inert solvent, for example tetramethylenesulfone, at temperatures of between approximately 80° and 150°, preferably at 120°. After conventional work-up the nitriles can be isolated directly.

Ethers of the formula I can be obtained by etherification of corresponding hydroxy compounds, in particular of the formula VI or VII, preferably corresponding Phenols, the hydroxy compound advantageously being converted first into an appropriate metal derivative, for example by treatment with NaH, $NaNH_2$, NaOH, KOH, $Na_2CO_3$ or $K_2CO_3$ into the corresponding alkali metal alcoholate or alkali metal phenolate. This can then be reacted with the corresponding alkyl halide, alkyl sulfonate or dialkyl sulfate, advantageously in an inert solvent such as acetone, 1,2-dimethoxyethane, DMF or dimethyl sulfoxide or else with an excess of aqueous or aqueous-alcoholic NaOH or KOH at temperatures of between approximately 20° and 100°.

For the preparation of nitriles of the formula I it is also possible to react corresponding chlorine, bromine or iodine compounds of the formula I with a cyanide, preferably with a metal cyanide such as NaCN, KCN or $Cu_2(CN)_2$, for example in the presence of pyridine in an inert solvent, for example DMF or N-methylpyrrolidone, at temperatures of between 20° and 200°.

Compounds of the formula I in which $A^1$ is substituted by at least one fluorine atom and/or one CN group can also be obtained from the corresponding diazonium salts by exchange of the diazonium group for a fluorine atom or for a CN group, for example by the methods of Schiemann or Sandmeyer.

Dioxane derivatives or dithiane derivatives of the formula I are advantageously prepared by reacting a corresponding aldehyde (or one of its reactive derivatives) with a corresponding 1,3-diol (or one of its reactive derivatives) or, respectively, with a corresponding 1,3-dithiol, preferably in the presence of an inert solvent such as benzene or toluene and/or a catalyst, for example a strong acid such as sulfuric acid, benzenesulfonic acid or p-toluenesulfonic acid, at temperatures between approximately 20° and approximately 150°, preferably between 80° and 120°. The principal reactive derivatives of the starting materials which are suitable are acetals.

The aldehydes and 1,3-diols or 1,3-dithiols mentioned and their reactive derivatives are in some cases known, while in other cases they can be prepared without difficulty, in accordance with standard methods of organic chemistry, from compounds known from the literature. For example, the aldehydes can be obtained by oxidation of corresponding alcohols or by reduction of nitriles or corresponding carboxylic acids or their derivatives, the diols by reduction of corresponding diesters, and the dithiols by reaction of corresponding dihalides using NaSH.

The liquid-crystalline media according to the invention preferably contain, in addition to one or more compounds according to the invention, from 2 to 40 further constituents, in particular from 4 to 30 components. With very particular preference these media contain, in addition to one or more compounds according to the invention, from 7 to 25 components. These further constituents are preferably selected from nematic or nematogenic (monotropic or isotropic ) substances, especially substances from the classes of the azoxybenzenes, benzylideneanilines, biphenyls, terphenyls, phenyl or cyclohexyl benzoates, phenyl or cyclohexyl cyclohexanecarboxylates, phenyl or cyclohexyl cyclohexyl benzoates, phenyl or cyclohexyl cyclohexylcyclohexanecarboxylates, cyclohexylphenyl benzoates, cyclohexylphenyl cyclohexanecarboxylates or cyclohexylphenyl cyclohexylcyclohexanecarboxylates, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

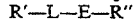

R'—L—E—R"   1

R'—L—COO—E—R"   2

R'—L—OOC—E—R"   3

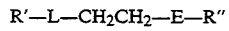

R'—L—CH₂CH₂—E—R"   4

R'—L—C≡C—E—R"   5

In the formulae 1, 2, 3, 4 and 5 L and E, which may be identical or different, are in each case independently of one another a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, in which Phe is 1,4-phenylene which is unsubstituted or substituted by fluorine, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

Preferably, one of the radicals L and E is Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group Cyc, Phe and Pyr and at the same time one or more components selected from the compounds of the formulae 1, 2, 3, 4 and 5 in which one of the radicals L and E is selected from the group Cyc, Phe and Pyr and the other radical is selected from the group —Phe—Phe—, —Phe—Cyc, —Cyc—Cyc—, —G—Phe— and —G—Cyc—, and, if desired, one or more components selected from the compounds of the formulae 1, 2, 3, 4 and 5 in which the radicals L and E are selected from the group —Phe—Cyc, —Cyc—Cyc—, —G—Phe— and —G—Cyc—.

In the compounds of the subformulae 1a, 2a, 3a, 4a and 5a, R' and R" are, in each case independently of one another, alkyl, alkenyl, alkoxy, alkenyloxy or alkanoyloxy, having up to 8 carbon atoms. In the majority of these compounds R' and R" are different from one another, with one of these radicals usually being alkyl or alkenyl. In the compounds of the subformulae 1b, 2b, 3b, 4b and 5b R" is —CN, —CF₃ —OCF₃, —OCHF₂, F, Cl or —NCS; in this case R has the meaning given in the case of the compounds of the subformulae 1a to 5a and is preferably alkyl or alkenyl. However, other variants of the substituents envisaged in the compounds of the formulae 1, 2, 3, 4 and 5 can also be employed. Many of these substances, or alternatively mixtures thereof, are commercially available. All of these substances are obtainable by methods known from the literature or in analogy thereto.

The media according to the invention preferably contain, in addition to components from the group of the compounds 1a, 2a, 3a, 4a and 5a (group 1), components from the group of the compounds 1b, 2b, 3b, 4b and 5b (group 2), the proportions of which are preferably as follows:

Group 1: from 20 to 90%, in particular from 30 to 90%,

Group 2: from 10 to 80%, in particular from 10 to 50%, the sum of the proportions of the compounds according to the invention and the compounds from groups 1 and 2 giving a result of 100%.

The media according to the invention preferably contain from 1 to 40%, particularly preferably from 5 to 30%, of compounds according to the invention. Of further preference are media which contain more than 40%, in particular from 45 to 90%, of compounds according to the invention. The media preferably contain three, four or five compounds according to the invention.

The media according to the invention are prepared in a manner known per se. Generally the components are dissolved with one another, advantageously at elevated temperature. By appropriate additions the liquid-crystalline phases according to the invention can be modified so that they can be used in all hitherto disclosed types of liquid-crystal display elements.

Additives of this kind are known to the person skilled in the art and are described in detail in the literature (H. Kelker/R. Hatz, Handbook of Liquid Crystals, Verlag Chemie, Weinheim, 1980). For example, pleochroic dyes can be added to produce colored guest-host systems or substances can be added to alter the dielectric anisotropy, the viscosity and/or the orientation of the nematic phases.

Even without further comments it is assumed that a person skilled in the art can utilize the above description in the widest context. The preferred embodiments are, therefore, merely to be interpreted as a descriptive disclosure which should in no way be interpreted as in any way limiting.

The complete disclosure content of all applications, patents and publications listed above and below, and of the corresponding application P 42 39 169, filed on 21.11.92, are incorporated into this application by reference. mp.=melting point, cp.=clear point. Above and below, percentages are percent by weight; all temperatures are given in degrees Celsius. "Conventional work-up" means: water is added, the mixture is extracted with methylene chloride, the phases are separated, the organic phase is dried and concentrated by evaporation, and the product is purified by crystallization and/or chromatography.

Further definitions:

C: solid crystalline state, S: smectic phase (the index indicates the phase type), N: nematic state, Ch: cholesteric phase, I: isotropic phase. The number between two symbols indicates the transition temperature in degrees Celsius.

| DAST | diethylaminosulfur trifluoride |
| --- | --- |
| DCC | dicyclohexylcarbodiimide |
| DDQ | dichlorodicyanobenzoquinone |
| DIBALH | diisobutylaluminum hydride |
| HMTAP | hexamethyltriaminophosphine |
| POT | potassium tert-butanolate |
| PCC | pyridinium chlorochromate |
| THF | tetrahydrofuran |
| TPP | triphenylphosphine |
| pTSOH | p-toluenesulfonic acid |

EXAMPLES

Example 1

Preparation of
3-(3,4,5-trifluorophenyl)-1-methylcyclobutane

A) 3,4,5-Trifluorovinylbenzene

A mixture of 1 mol of 3,4,5-trifluorobromobenzene and 3 l of THF is admixed at −70° C. with 1 mol of BuLi. Subsequently, a mixture of 0.5 mol of zinc bromide in 1 l of THF is added to the reaction mixture, and this mixture is stirred for 30 minutes at −65° C. Then 1 mol of vinyl bromide and 0.022 mol of nickel(II) chloride/TPP is added.

The reaction mixture is stirred for 16 hours at room temperature and worked up in the conventional way. The resulting styrene derivative is processed further without purification.

B) 3-(3,4,5,-Trifluorophenyl)-2,2-dichlorocyclobutanone

A mixture of 0.25 mol of 1A, 23.0 g of zinc-copper (3% copper) and 800 ml of diethyl ether is admixed over the course of 15 minutes with 0.25 ml of trichloroacetyl chloride and the mixture is subsequently stirred under reflux for 8 hours. After conventional work-up the product is obtained, which is processed further without purification.

C) 3-(3,4,5,-Trifluorophenyl)cyclobutanone

A mixture of 0.144 mol of 1B, 0.53 mol of zinc powder and 880 ml of glacial acetic acid is stirred at room temperature for 17 hours. After conventional work-up the product is obtained, which is processed further without purification.

D) 3-(3,4,5,-(Trifluorophenyl)-1-methylenecyclobutane [sic]

A mixture of 0.15 mol of triphenylmethylenephosphine, 100 ml of tetraglyme and 0.13 mol of 1C [lacuna] added and stirred at room temperature for 16 hours. After conventional work-up and distillation from 100 ml of ethanol/ethyl acetate the pure product is obtained.

E) A mixture of 0.1 mol of 1D, 1 mmol of Pd/C (10%) and 100 ml of toluene is hydrogenated to saturation at room temperature. After conventional work-up and chromatography the pure product is obtained.

The following are prepared analogously:
3-(3,4-Difluorophenyl)-1-methylcyclobutane
3-(4-Trifluoromethoxyphenyl)-1-methylcyclobutane
3-(3,5-Difluoro-4-difluoromethoxyphenyl)-1-methylcyclobutane
3-(3,4,5-Trifluorophenyl)-1-ethylcyclobutane
3-(3,4,5-Trifluorophenyl)-1-propylcyclobutane
3-(3,4,5-Trifluorophenyl)-1-butylcyclobutane
3-(3,4,5-Trifluorophenyl)-1-pentylcyclobutane
3-(3,4,5-Trifluorophenyl)-1-hexylcyclobutane
3-(3,4,5-Trifluorophenyl)-1-heptylcyclobutane
3-(3,4-Difluorophenyl)-1-ethylcyclobutane
3-(3,4-Difluorophenyl)-1-propylcyclobutane
3-(3,4-Difluorophenyl)-1-butylcyclobutane
3-(3,4-Difluorophenyl)-1-pentylcyclobutane
3-(3,4-Difluorophenyl)-1-hexylcyclobutane
3-(3,4-Difluorophenyl)-1-heptylcyclobutane
3-(-trans-4-(3,4,5-Trifluorophenyl)cyclohexyl]-1-methylcyclobutane [sic]
3-(-trans-4-(3,4,5-Trifluorophenyl)cyclohexyl]-1-ethylcyclobutane [sic]
3-(-trans-4-(3,4,5-Trifluorophenyl)cyclohexyl]-1-propylcyclobutane [sic]
3-(-trans-4-(3,4,5-Trifluorophenyl)cyclohexyl]-1-butylcyclobutane [sic]
3-(-trans-4-(3,4,5-Trifluorophenyl)cyclohexyl]-1-pentylcyclobutane [sic]
3-(-trans-4-(3,4,5-Trifluorophenyl)cyclohexyl]-1-hexylcyclobutane [sic]
3-(-trans-4-(3,4,5-Trifluorophenyl)cyclohexyl]-1-heptylcyclobutane [sic]

Example 2

6-(3,4,5-Trifluorophenyl)-2-methylspiro[3.3]heptane 2A) 7-(3,4,5-Trifluorophenyl)-1,1-dichlorospiro[3.3]-heptan-2-one 0.1 mol of 1D is reacted in accordance with Example 1B with 0.1 mol of trichloroacetyl chloride. After conventional work-up the product is obtained, which is processed further without purification.

2B) 6-(3,4,5-Trifluorophenyl)spiro[3.3]heptan-2-one

A mixture of 0.075 mol of 2A and 0.25 mol of zinc powder is reacted in accordance with Example 1C.

2C  6-(3,4,5-Trifluorophenyl)-2-methylenespiro[3.3]-heptane 0.05 mol of 2B is reacted in accordance with Example 1D with 0.06 mol of triphenylphosphine. After conventional work-up and purification by chromatography the product is obtained.

2D) 0.02 mol of 2C is hydrogenated in accordance with Example 1E.

The following are prepared analogously:
6-(3,4-Difluorophenyl)-2-methylspiro[3.3]heptane
6-(4-Trifluoromethoxyphenyl)-2-methylspiro[3.3]heptane [sic]
6-(3,5-Difluoro-4-difluoromethoxyphenyl)-2-methylspiro-[3.3]heptane
6-(3,4,5-Trifluorophenyl)-2-ethylspiro[3.3]heptane 6-(3,4,5-Trifluorophenyl)-2-propylspiro[3.3]heptane, C 9 I
6-(3,4,5-Trifluorophenyl)-2-butylspiro[3.3]heptane
6-(3,4,5-Trifluorophenyl)-2-pentylspiro[3.3]heptane, C 11 I
6-(3,4,5-Trifluorophenyl )-2-hexylspiro[3.3]heptane
6-(3,4,5-Trifluorophenyl )-2-heptylspiro[3.3]heptane
6-(3,4-Difluorophenyl)-2-ethylspiro[3.3]heptane
6-(3,4-Difluorophenyl)-2-propylspiro[3.3]heptane
6-(3,4-Difluorophenyl)-2-butylspiro[3.3]heptane
6-(3,4-Difluorophenyl)-2-pentylspiro[3.3]heptane
6-(3,4-Difluorophenyl)-2-hexylspiro[3.3]heptane
6-(3,4-Difluorophenyl)-2-heptylspiro[3.3]heptane 6-[trans-4-(3,4,5-Trifluorophenyl]cyclohexyl]-2-methyl-spiro[3.3]heptane [sic]
6-[trans-4-(3,4,5-Trifluorophenyl]cyclohexyl]-2-ethyl-spiro[3.3]heptane [sic], C 62 I
6-[trans-4-(3,4,5-Trifluorophenyl]cyclohexyl]-2-propyl-spiro[3.3]heptane [sic], C 47 N (44.7) I
6-[trans-4-(3,4,5-Trifluorophenyl]cyclohexyl]-2-butyl-spiro[3.3]heptane [sic], C 56 I
6-[trans-4-(3,4,5-Trifluorophenyl]cyclohexyl]-2-pentyl-spiro[3.3]heptane [sic], C 55 N (41.5) I
6-[trans-4-(3,4,5-Trifluorophenyl]cyclohexyl]-2-hexyl-spiro[3.3]heptane [sic]
6-[trans-4-(3,4,5-Trifluorophenyl]cyclohexyl]-2-heptyl-spiro[3.3]heptane [sic]

6-(3,4,5-Trifluorobiphenyl-4'-yl)-2-methylspiro[3.3]-heptane
6-(3,4,5-Trifluorobiphenyl-4'-yl)-2-ethylspiro[3.3]-heptane
6-(3,4,5-Trifluorobiphenyl-4'-yl)-2-propylspiro[3.3]-heptane, C 27 N (12.1) I 8-[(3,4,5-Trifluorophenyl)cyclohexyl)]-2-propyldispiro-[3.1.1.3]decane, C 41 N (43.5) I 6-(4-Ethoxyphenyl)-2-propylspiro[3.3]heptane, C 6 N (4.9) I
6-(4-Ethoxyphenyl)-2-butylspiro[3.3]heptane
6-(4-Ethoxyphenyl)-2-ethylspiro[3.3]heptane
6-(4-Ethoxyphenyl)-2-methylspiro[3.3]heptane 6-(4-Methoxyphenyl)-2-propylspiro[3.3]heptane
6-(4-Methoxyphenyl)-2-butylspiro[3.3]heptane
6-(4-Methoxyphenyl)-2-ethylspiro[3.3]heptane
6-(4-Methoxyphenyl)-2-methylspiro[3.3]heptane
6-(4-Propoxyphenyl)-2-propylspiro[3.3]heptane
6-(4-Pentylphenyl)-2-propylspiro[3.3]heptane

Example 3

7-(3,4,5-Trifluorophenyl)-2-methylspiro[3.5]nonane 3A) 7-(3,4,5-Trifluorophenyl)-1,1-dichlorospiro[3.5]-nonane 0.1 mol of 4-methylene-1-(3,4,5-trifluorophenyl)-cyclohexane (obtainable by reacting 3,4,5-trifluorophenylmagnesium bromide with the monoethylene ketal of cyclohexane-1,4-dione followed by elimination of water, hydrogenation and ketal cleavage) and 0.1 mol of trichloroacetyl chloride are reacted in accordance with Example 1B.

After reaction with zinc in accordance with Example 1C and with triphenylmethylene phosphine in accordance with Example 1D and hydrogenation in accordance with Example 1E the product is obtained.

The following are prepared analogously:
7-(3,4-Difluorophenyl)-2-methylspiro[3.5]nonane
7-(3,4-Difluorophenyl)-2-propylspiro[3.5]nonane
7-(3,4-Difluorophenyl)-2-pentylspiro[3.5]nonane
7-(3,4,5-Trifluorophenyl)-2-pentylspiro[3.5]nonane, C 3 I
7-[trans-4-(3,4,5-Trifluorophenyl)cyclohexyl]-2-methylspiro[3.5]nonane
7-[trans-4-(3,4,5-Trifluorophenyl)cyclohexyl]-2-propyl-spiro[3.5]nonane
7-[trans-4-(3,4,5-Trifluorophenyl)cyclohexyl]-2-pentyl-spiro[3.5]nonane

Example 4

6-(3,4,5-Trifluorophenyl)-2-(trans-4-propylcyclohexyl)-spiro[ 3.3]heptane 4A) 3-(trans-4-Propylcyclohexyl)-2,2-dichlorocyclobutanone A mixture of 0.25 mol of trans-4-propyl-1-vinylcyclohexane (prepared according to WO 88/02357) and 800 ml of diethyl ether is reacted with trichloroacetyl chloride in accordance with Example 1B.

4B ) 3-(trans-4-Propylcyclohexyl)cyclobutanone 0.1 mol of 4A is treated with 0.4 mol of zinc powder in analogy to Example 1C.

4C ) 3-(trans-4-Propylcyclohexyl)-1-methylenecyclobutane 0.05 mol of 4B is reacted with 0.07 mol of triphenylmethylenephospine in analogy to Example 1D.

4D ) 2-(trans-4-Propylcyclohexyl)-5,5-dichlorospiro[3.3]-heptan-6-one [sic]

35 mmol of 4C are reacted with trichloroacetyl chloride in analogy to Example 1B.

4E) 2-(trans-4-Propylcyclohexyl)spiro[3.3]heptan-6one 25 mmol of 4D are treated with zinc in analogy to Example 1C.

4F) 2-(trans-4-Propylcyclohexyl)-6-hydroxy-6-(3,4,5-trifluorophenyl)spiro[3.3]heptane A mixture of 15 mmol of 3,4,5-trifluorophenylmagnesium bromide (prepared from 3,4,5-trifluorobromobenzene and magnesium turnings), 15 mmol of 4E and 50 ml of diethyl ether is stirred for 15 hours. After conventional work-up the product is obtained, which is processed further without purification.

4G) 2-(trans-4-Propylcyclohexyl)-6-(3,4,5-trifluorophenyl)spiro[3.3]hept-5-ene

A mixture of 12 mmol of 4F, 100 ml of toluene and 0.5 g of p-toluenesulfonic acid is heated on a water separator for 10 hours. After conventional work-up the product is obtained, which is processed further without purification.

4H) 10 mmol of 4G are hydrogenated in accordance with Example 1E. After conventional work-up the product is obtained, C 46 N (61.4) I.

The following are prepared analogously:
6-(3,4-Difluorophenyl)-2-(trans-4-propylcyclohexyl)-spiro-[3.3]heptane
6-(3,4-Difluorophenyl)-2-(trans-4-ethylcyclohexyl)-spiro-[3.3]heptane
6-(3,4,5-Trifluorophenyl)-2-(trans-4-ethylcyclohexyl)-spiro[3.3]heptane
6-(4-Trifluoromethoxyphenyl)-2-(trans-4-propylcyclohexyl)spiro[3.3]heptane, C 67 N (95.2) I
(6-(4-Difluoromethoxy-3,5-difluorophenyl)-2-(trans-4-propylcyclohexyl)spiro[3.3]heptane [sic], C 43 N (77.5) I 6-(4-Cyanophenyl)-2-(trans-4-propylcyclohexyl)-spiro[3.3]-heptane, C 113 N (162) I
6-(4-Ethoxyphenyl)-2-(trans-4-propylcyclohexyl)-spiro[3.3]heptane
Example 5
10.0% 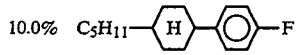
8.0% 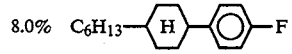
6.0% 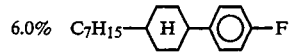
8.0% 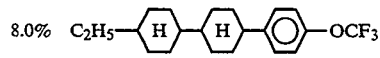
12.0% 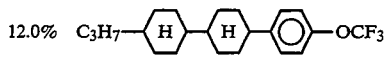
9.0% 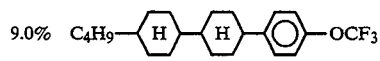
9.0% 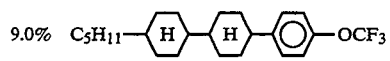
12.0% 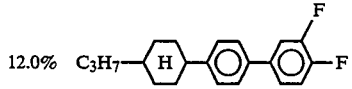
10.0% 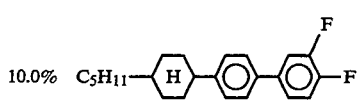
5.0% 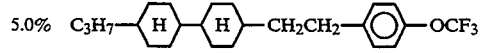
5.0% 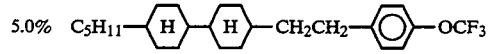
2.0% 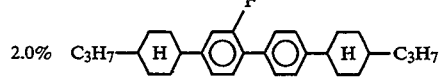
2.0% 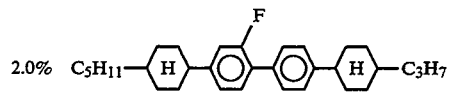
2.0% 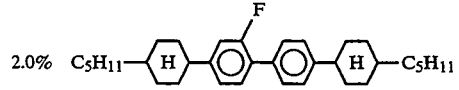
are added in each case one of the following compounds:
(a) 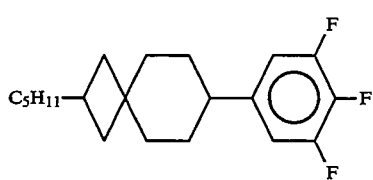
(b) 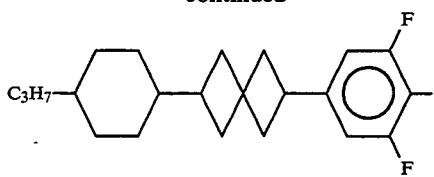
(c) 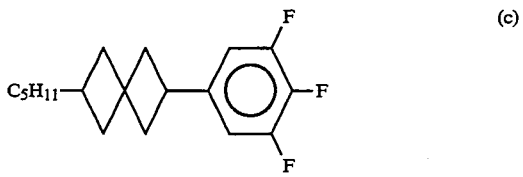
(d) 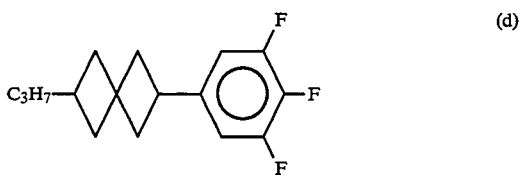
(e) 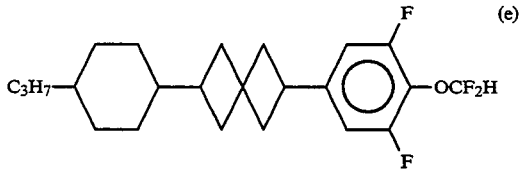
(f) 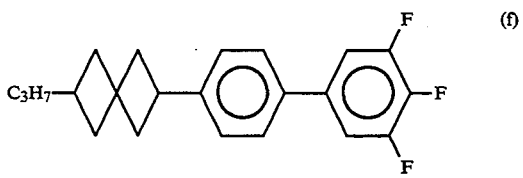
(g) 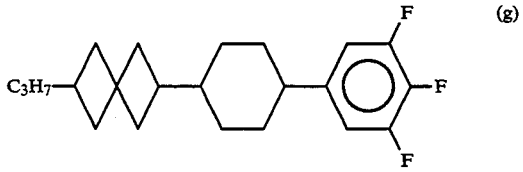
(h) 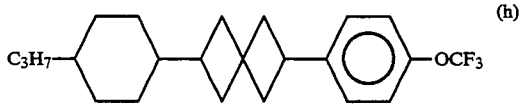
(i) 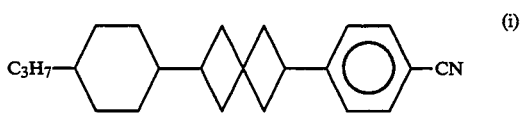
(j) 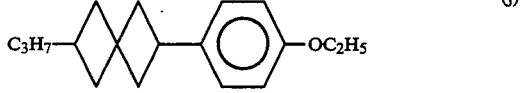
(k) 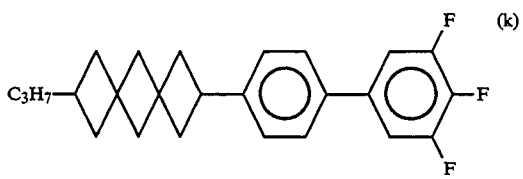

The physical data of the resulting mixtures can be taken from Table I:

TABLE I

| | Clear Point (°C.) | Δε | Δn | Viscosity (mm² · s⁻¹) |
|---|---|---|---|---|
| B | 91 | +5.2 | 0.094 | 15.0 |
| B + (a) | 71 | n.m. | 0.085 | 15.8 |
| B + (b) | 86 | 5.5 | 0.092 | 14.8 |
| B + (c) | 69 | 5.0 | 0.084 | 14.2 |
| B + (d) | 68 | 5.2 | 0.084 | 13.9 |
| B + (e) | 87 | 5.4 | 0.092 | 15.6 |
| B + (f) | 83 | 5.8 | 0.097 | 14.9 |
| B + (g) | 83 | 5.5 | 0.091 | 15.0 |
| B + (h) | 90 | 5.2 | 0.094 | 14.4 |
| B + (i) | 98 | 6.2 | 0.102 | 17.7 |
| B + (j) | 80 | 4.5 | 0.092 | 14.2 |
| B + (k) | 84 | 5.4 | 0.091 | 15.4 |

The compounds according to the invention generally achieve a lower optical anisotropy, a lower clear point and a lower viscosity.

We claim:

1. A cyclobutane benzene compound of formula I

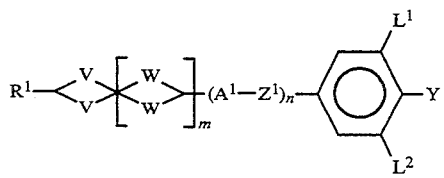

in which
R¹ is alkyl or alkenyl having 1 to 16 carbon atoms, in which additionally one or more CH₂ groups may be replaced by —O—, or is a group of the formula

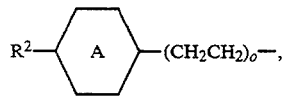

in which
R² is alkyl or alkenyl having 1 to 16 carbon atoms,

A is 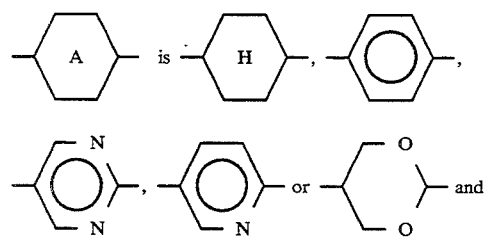 and o is 0 or 1,
V and W are each CH₂ or CH₂CH₂, and when V is CH₂CH₂ m is 1, 2 or 3 and W is CH₂,
A¹ is each independently 1,4-phenylene which is unsubstituted or substituted by 1 to 2 fluorine atoms, in which, in addition, one or two CH groups may be replaced by N, or is 1,4-cyclohexylene which is unsubstituted or substituted by a cyano group, and in which, in addition, one or two CH₂ groups may be replaced by O or S, or is thiadiazole-2,5-diyl, 1,4-bicyclo[2.2.2]octylene, or a radical of the formula

in which r and s are each 0, 1, 2 or 3,
L¹ and L² are each F,
Z¹ is —CO—O, —O—CO—, —CH₂O—, —OCH₂—, —CH₂CH₂—, —C≡C— or a single bond,
Y is NCS, halogen or an alkyl, alkoxy, alkenyl or alkenyloxy group having 1 to 8 carbon atoms which is substituted by at least one fluorine and/or chlorine atom, and, if m=1, 2 or 3, is CN, or alkyl or alkenyl having up to 16 carbon atoms, in which, in addition, 1 or more CH₂ groups may be replaced by —O—,
m is 0, 1, 2 or 3, and
n is 0, 1 or 2.

2. A compound according to claim 1, in which m is 0.
3. A compound according to claim 1, in which V is CH₂.
4. A compound according to claim 3, of the formula

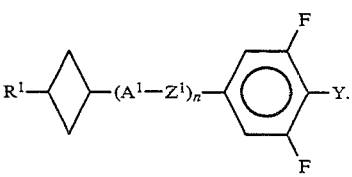

5. A compound according to claim 4, of the formula I2

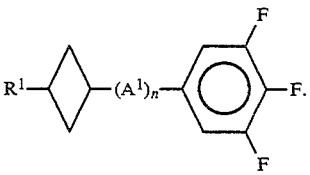

6. A compound according to claim 1, of the formula I3

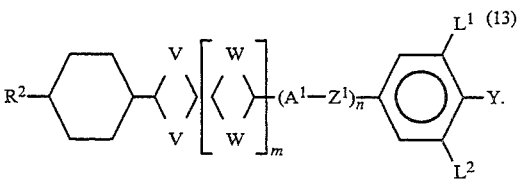

7. A compound according to claim 6, of the formula

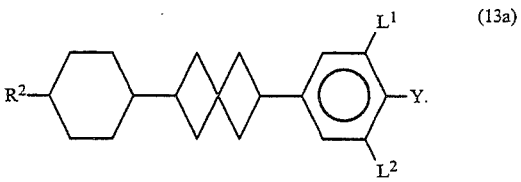

8. A liquid-crystalline medium containing at least two liquid-crystalline components, wherein at least one component is at least one compound of formula I according to claim 1.

9. An electrooptical display containing a liquid-crystalline medium according to claim 8.

10. A spiro heptane benzene compound of formula I′

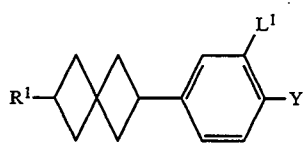

wherein

R¹ is alkyl or alkenyl having 1 to 16 carbon atoms, in which additionally one or more CH₂ groups may be replaced by —O—, or is a group of the formula

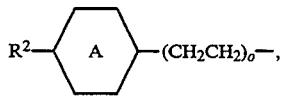

in which R² is alkyl or alkenyl having 1 to 16 carbon atoms,

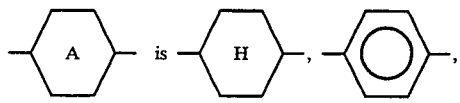

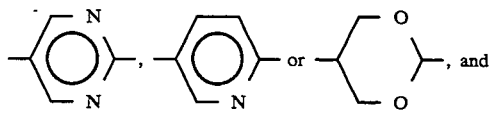

o is 0 or 1;

Y is NCS, halogen or an alkyl, alkoxy, alkenyl or alkenyloxy group having 1 to 8 carbon atoms which is substituted by at least one fluorine and/or chlorine atom, CN, or alkyl or alkenyl having up to 16 carbon atoms, in which one or more CH₂ groups are optionally replaced by O; and L¹ is H or F.

11. A liquid-crystalline medium containing at least two liquid-crystalline components, wherein at least one component is at least one compound of formula I′ according to claim 10.

12. An electrooptical display containing a liquid-crystalline medium according to claim 11.

* * * * *